(12) United States Patent
Pepper (10) Patent No.: US 8,486,103 B2
(45) Date of Patent: *Jul. 16, 2013

(54) BALLOON DILATION CATHETER HAVING TRANSITION FROM COAXIAL LUMENS TO NON-COAXIAL MULTIPLE LUMENS

(75) Inventor: Lanny R. Pepper, Larue, TX (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/188,054

(22) Filed: Jul. 21, 2011

(65) Prior Publication Data

US 2011/0282377 A1 Nov. 17, 2011

Related U.S. Application Data

(63) Continuation of application No. 12/399,830, filed on Mar. 6, 2009, now Pat. No. 7,985,235, which is a continuation of application No. 11/158,855, filed on Jun. 22, 2005, now Pat. No. 7,500,982.

(51) Int. Cl.
*A61M 29/00* (2006.01)
(52) U.S. Cl.
USPC .......................................... 606/194; 604/103

(58) Field of Classification Search
USPC .................... 604/103, 103.1, 103.4; 606/194
See application file for complete search history.

(56) References Cited

U.S. PATENT DOCUMENTS

| | | | |
|---|---|---|---|
| 6,905,477 B2* | 6/2005 | McDonnell et al. | 604/103.04 |
| 2004/0059291 A1* | 3/2004 | McDonnell et al. | 604/103.04 |
| 2004/0220515 A1* | 11/2004 | Constantz | 604/43 |
| 2005/0059955 A1* | 3/2005 | Delaney et al. | 604/509 |
| 2005/0107819 A1* | 5/2005 | Sater | 606/194 |
| 2005/0113803 A1* | 5/2005 | Duffy | 604/528 |

* cited by examiner

*Primary Examiner* — Victoria P Shumate
(74) *Attorney, Agent, or Firm* — King & Schickli, PLLC

(57) ABSTRACT

A shaft for a balloon dilation catheter comprises a proximal portion wherein a guidewire tubular member is disposed coaxially within an outer tubular member, a shaft transitional portion, wherein the guidewire member is disposed within the outer member, with at least one distal tubular member not present in the proximal portion, a shaft distal portion, wherein the guidewire member and the distal members are disposed side-by-side and encased within a distal body, and fluid-tight barrier within a proximal lumen blocking the flow of fluid in the proximal lumen, but allowing the proximal lumen to remain in fluid communication with a distal lumens.

20 Claims, 4 Drawing Sheets

BALLOON DILATION CATHETER HAVING TRANSITION FROM COAXIAL LUMENS TO NON-COAXIAL MULTIPLE LUMENS

CROSS-REFERENCE TO RELATED APPLICATIONS

This application is a Continuation of U.S. patent application Ser. No. 12/399,830, filed Mar. 6, 2009 now U.S. Pat. No. 7,985,235, which is a Continuation of U.S. patent application Ser. No. 11/158,855, entitled "BALLOON DILATION CATHETER HAVING TRANSITION FROM COAXIAL LUMENS TO NON-COAXIAL MULTIPLE LUMENS," filed Jun. 22, 2005, now U.S. Pat. No. 7,500,982, issued Mar. 10, 2009.

TECHNICAL FIELD

The current invention relates generally to angioplasty apparatus, and more specifically to balloon dilation catheters. In particular, it relates to a balloon dilation catheter having a first portion wherein the guidewire lumen and the balloon inflation/deflation lumen are coaxial and a second portion wherein the guidewire lumen and the balloon inflation/deflation lumens are non-coaxial.

BACKGROUND

As treatment using balloon dilation catheters, for example, Percutaneous Transluminal Angioplasty Catheters (i.e., "PTACs"), has progressed into narrower and more remote vessels within the body, this has necessitated the use of catheters having correspondingly smaller shaft diameters and longer shaft lengths. However, this migration towards catheters with smaller diameter, longer shafts has produced several new problems of its own. First, catheter inflation/deflation time performance (i.e., the time required for inflation and deflation of the balloon) has suffered (i.e., increased) in the longer, smaller diameter catheters as frictional resistance to movement of the inflation fluid through the balloon inflation/deflation lumen(s) of the catheter becomes significant. Second, accessing increasingly smaller body lumens requires that the distal portion of the catheter shaft have sufficient longitudinal flexibility to follow the guidewire as it twists and turns through the smaller, more arduous pathways in the body. If the distal end of the catheter is not flexible enough, it may pull the guidewire out of position in the target lumen rather than follow it. The flexibility of the distal portion of the catheter is often referred to as the "trackability" of the catheter.

Further, the operating pressure of dilation balloons continues to rise. Whereas at one time a balloon inflation pressure of 10 atmospheres was considered high, now balloons having operating pressures of up to 30 atmospheres are known, and it is foreseeable that even higher pressures may be utilized in the near future. It will be appreciated that use of such high pressure balloons requires the use of catheters having correspondingly high pressure ratings for their inflation/deflation lumens.

One conventional approach to improving inflation/deflation time in PTAC and other balloon catheter shafts is the so-called coaxial design, wherein two concentrically disposed tubular members form the catheter shaft. In coaxial catheters, the inside of the inner tubular member is used for the guidewire lumen, the outer tubular member is used for the catheter shaft body, and the annular space between the outer surface of the inner tubular member and the inner surface of the outer tubular member forms a inflation/deflation lumen for transporting contrast media or other non-compressible fluid for inflating and deflating the balloon. In such coaxial catheters, the inflation/deflation performance is governed by the difference in cross-sectional area between the inside diameter of the outer tubular member and the outside diameter of the inner tubular member in conjunction with the length of the shaft. For a given combination of overall catheter diameter and guidewire lumen diameter, the coaxial design is considered to maximize the cross-sectional area available for the inflation/deflation lumen, thereby providing the best inflation/deflation performance for a given length catheter.

Unfortunately, while the inflation/deflation time performance of coaxial designs is considered good, the trackability of such designs tends to be poor because of the inherent stiffness of the full-diameter outer tubular member. It will be appreciated that, generally speaking, a larger diameter tube will exhibit greater stiffness than a smaller diameter tube made of the same material. Further, as balloon working pressures increase, the outer tubular member must have thicker and/or stronger walls to withstand the pressure. Thus, as the pressure rating of a coaxial style catheter increases to handle higher-pressure balloons, its trackability characteristics tend to become even worse.

In an effort to provide better trackability, it is known to produce balloon catheter shafts wherein the guidewire lumen and the inflation/deflation lumens are separate and non-coaxial. Such non-coaxial designs are often referred-to in the industry as "multi-lumen" catheters, even though it is appreciated that the coaxial designs effectively have multiple lumens as well. In keeping with industry practice, for purposes of this application, the term "multi-lumen" will refer to designs wherein the guidewire lumen and inflation/deflation lumen(s) are not coaxial. There are currently two main types of multi-lumen catheter shafts: dual lumen shafts and extruded dual port shafts. In dual lumen shafts, a first tubular member forming the guidewire lumen therewithin and a second tubular member forming the inflation/deflation lumen therewithin run parallel to one another within a full-diameter outer jacket surrounding both lumens. Since only the guidewire lumen member and the inflation/deflation lumen member (i.e., not the outer jacket) are exposed to the balloon inflation pressure, then only these relatively small diameter tubular members need to be strong enough withstand such pressures, and the full-diameter outer jacket of the catheter can be made of a relatively soft, flexible material. This combination of smaller diameter (and hence more flexible) high-pressure tubular lumen members and a softer full-diameter casing gives dual lumen catheter shafts significantly more flexibility and trackability than coaxial designs.

The other type of multi-lumen catheter shaft, i.e., the extruded dual port shaft, has guidewire and inflation/deflation lumens that are integrally formed longitudinal voids created during extrusion of the plastic or resin catheter shaft. These extruded shafts tend to have good trackability, especially when extruded from relatively soft plastic/resin, due to their lack of any internal structural stiffeners. Further, their extruded construction allows the inflation/deflation lumen to be non-circular in shape, e.g., semi-circular or even crescent-shaped, to increase the portion of the catheter's total cross-sectional area that is available for the inflation/deflation lumen. However, unless the lumen members are lined with a stronger material, the maximum balloon inflation pressure rating of extruded dual port shafts tends to be low compared to other designs. Increasing the strength of the plastic/resin used for the extruded body will improve the pressure rating, but only at the expense of trackability. For this reason, the use of extruded dual port catheters becomes more problematic as the working pressure of balloons rises.

Regrettably, while multi-lumen catheter shafts exhibit improved trackability over the coaxial designs previously described, both types of multi-lumen catheter shafts have inflation/deflation time performance that is inferior to the coaxial designs. The reduced-size inflation/deflation lumens of the multi-lumen designs simply do not have fluid flow characteristics that are as good as the annular inflation/deflation lumen of the coaxial designs. Accordingly, practitioners are currently forced to choose between balloon catheters, which have good inflation/deflation performance but inferior trackability, good trackability but inferior inflation/deflation time performance, or a less-than-optimum compromise on both characteristics.

A need therefore exists, for a balloon catheter with a shaft having inflation/deflation time performance similar to that of a conventional coaxial design, but with improved trackability in the distal portion.

SUMMARY

The present invention disclosed and claimed herein comprises, in one aspect thereof, a balloon dilation catheter adapted to be utilized with a guidewire. The catheter comprises an elongated catheter shaft and a balloon. The catheter shaft has a shaft proximal portion, a shaft distal portion, and a shaft transitional portion disposed therebetween. Each of the proximal, distal and transitional shaft portions has a proximal end and a distal end. The balloon has a proximal end and a distal end, the proximal end of the balloon being attached to the distal end of the shaft distal portion. The catheter shaft includes an outer tubular member having a bore and extending from the proximal end of the shaft proximal portion to the distal end of the shaft transitional portion. The shaft further includes a plurality of distal tubular members, each distal tubular member having a bore and extending from a starting point disposed within the shaft transitional portion to the distal end of the shaft distal portion. The portions of the distal tubular members extending between the starting point and the distal end of the shaft transitional portion are disposed within the bore of the outer tubular member. The bores of the distal tubular members define distal inflation/deflation lumens providing fluid communication between the shaft transition portion and the interior of the balloon. A distal body encases the portions of the distal tubular members extending between the distal end of the shaft transitional portion and the distal end of the shaft distal portion. The shaft further includes a guidewire tubular member having a bore and extending from the proximal end of the shaft proximal portion to the distal end of the balloon. The portion of the guidewire tubular member extending between the proximal end of the shaft proximal portion and the distal end of the shaft proximal portion is disposed coaxially within the bore of the outer tubular member, the portion of the guidewire tubular member extending between the distal tubular member starting point in the shaft transitional portion and the distal end of the shaft transitional portion is disposed within the bore of the outer tubular member alongside the distal tubular members, the portion of the guidewire tubular member extending between the distal end of the shaft transitional portion and the distal end of the shaft distal portion is disposed in a multi-lumen arrangement with the distal tubular members and encased in the distal body, and the portion of the guidewire tubular member extending from the distal end of the shaft distal portion to the distal end of the balloon passes through the interior of the balloon and is connected to the distal end of the balloon. The bore of the guidewire tubular member defines a guidewire lumen for conveying a guidewire through the catheter shaft and the balloon and the space between the exterior of the guidewire tubular member and the interior of the outer tubular member defines a proximal inflation/deflation lumen providing fluid communication between the shaft proximal portion and the shaft transitional portion. The shaft further includes a fluid-tight barrier disposed within the proximal inflation/deflation lumen between the distal tubular member starting point in the shaft transitional member and the distal end of the shaft transitional member. The fluid-tight barrier blocks the flow of inflation fluid past the shaft transitional portion in the proximal inflation/deflation lumen, but allows the proximal inflation/deflation lumen to remain in fluid communication with the distal inflation/deflation lumens.

The present invention disclosed and claimed herein comprises, in another aspect thereof, a shaft for a balloon dilation catheter to be utilized with a guidewire. The shaft comprises a shaft proximal portion, a shaft distal portion, and a shaft transitional portion disposed therebetween. Each of the proximal, distal and transitional shaft portions has a proximal end and a distal end. An outer tubular member having a bore extends from the proximal end of the shaft proximal portion to the distal end of the shaft transitional portion. At least one distal tubular member, each having a bore, extends from a starting point disposed within the shaft transitional portion to the distal end of the shaft distal portion. The portions of the distal tubular members extending between the starting point and the distal end of the shaft transitional portion are disposed within the bore of the outer tubular member. The bores of the distal tubular members define distal inflation/deflation lumens providing fluid communication between the shaft transition portion and the distal end of the shaft distal portion. A distal body encases the portions of the distal tubular members extending between the distal end of the shaft transitional portion and the distal end of the shaft distal portion. A guidewire tubular member having a bore extends from the proximal end of the shaft proximal portion to a point beyond the distal end of the shaft distal portion. The portion of the guidewire tubular member extending between the proximal end of the shaft proximal portion and the distal end of the shaft proximal portion is disposed coaxially within the bore of the outer tubular member, the portion of the guidewire tubular member extending between the distal tubular member starting point in the shaft transitional portion and the distal end of the shaft transitional portion is disposed within the bore of the outer tubular member alongside the distal tubular members, and the portion of the guidewire tubular member extending between the distal end of the shaft transitional portion and the distal end of the shaft distal portion is disposed in a multi-lumen arrangement with the distal tubular members and encased in the distal body. The bore of the guidewire tubular member defines a guidewire lumen for conveying a guidewire through the catheter shaft, and the space between the exterior of the guidewire tubular member and the interior of the outer tubular member defines a proximal inflation/deflation lumen providing fluid communication between the shaft proximal portion and the shaft transitional portion. A fluid-tight barrier is disposed within the proximal inflation/deflation lumen between the distal tubular member starting point in the shaft transitional member and the distal end of the shaft transitional member. The fluid-tight barrier blocks the flow of inflation fluid past the shaft transitional portion in the proximal inflation/deflation lumen, but allows the proximal inflation/deflation lumen to remain in fluid communication with the distal inflation/deflation lumens.

The present invention disclosed and claimed herein comprises, in a further aspect thereof, a shaft for a balloon dilation catheter to be utilized with a guidewire. The shaft comprises a shaft proximal portion wherein a guidewire tubular member having a first diameter and a first bore is disposed coaxially within an outer tubular member having a second diameter and a second bore. Connected to the distal end of the shaft proximal portion is a shaft transitional portion, wherein the guidewire tubular member is disposed within the bore of the outer tubular member and at least one distal tubular member having a third diameter and a third bore and not being present in the shaft proximal portion is also disposed within the bore of the outer tubular member, but not within the bore of the guidewire tubular member. Connected to the distal end of the shaft transitional portion is a shaft distal portion, wherein the guidewire tubular member and the distal tubular members are disposed in a side-by-side configuration and encased within a distal body, and the outer tubular member is not present. The bore of the guidewire tubular member defines a guidewire lumen for conveying a guidewire through the shaft, and the bores of the distal tubular members define distal inflation/deflation lumens providing fluid communication between the shaft transition portion and a distal end of the shaft distal portion. The space in the shaft proximal and transitional portions between the exterior of the guidewire tubular member and the interior of the outer tubular member defines a proximal inflation/deflation lumen providing fluid communication between a proximal end of the shaft proximal portion and the shaft transitional portion. A fluid-tight barrier is disposed within the proximal inflation/deflation lumen between a proximal end of the distal tubular members and a distal end of the outer tubular member. The fluid-tight barrier blocks the flow of inflation fluid past the shaft transitional portion in the proximal inflation/deflation lumen, but allows the proximal inflation/deflation lumen to remain in fluid communication with the distal inflation/deflation lumens.

DETAILED DESCRIPTION

The current invention is described below in greater detail with reference to certain preferred embodiments illustrated in the accompanying drawings.

Figure 1:
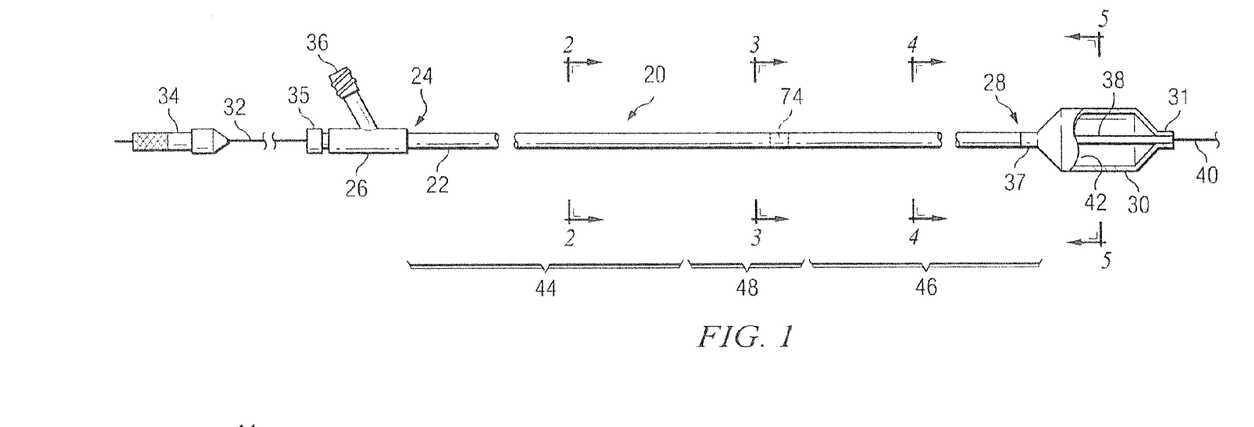
FIG. 1 is a side view of a balloon dilation catheter in accordance with a first embodiment.

Referring now to FIG. 1, there is illustrated a balloon dilation catheter in accordance with one embodiment of the current invention. While this design may be used to make catheters of any diameter, it is particularly suitable for small diameter catheters, e.g., those having a diameter of 5 French or smaller. The catheter 20 includes a shaft 22 having a proximal end 24 that may be affixed to an access fitting 26 and a distal end 28 that may be affixed to a dilation balloon 30. As explained in further detail below, a plurality of tubular members disposed within the catheter 20 define a plurality of internal passageways, known as lumens. One such tubular member, the guidewire tubular member, extends longitudinally through the catheter from the access fitting 26 to the distal end 31 of the balloon 30. The guidewire tubular member has a bore defining a guidewire lumen that allows a conventional guidewire 32 to be threaded through the interior of the catheter. A guidewire manipulator or "torquer" 34 may be secured to the guidewire 32 for rotating the guidewire from the proximal end of the catheter. Other tubular members within the catheter shaft 22 define inflation/deflation lumens that convey contrast liquid or other non-compressible inflation fluids through the shaft to and from the balloon, thereby allowing the balloon to be selectively inflated and deflated. The access fitting 26 may be of conventional design, having a first port 35 allowing the guidewire 32 to pass into and out of the guidewire lumen, and a second port 36 in fluid communication with the shaft's inflation/deflation lumens.

The dilation balloon 30 may be of conventional construction and is typically formed of relatively non-distensible plastic or polymer material. The envelope of the balloon may be plain or reinforced with longitudinal and/or circumferential filaments. For purposes of illustration, the balloon 30 is shown in its inflated configuration in FIG. 1, with portions of the envelope broken away to better illustrate the interior structure. Although not shown in a folded configuration, it will be appreciated that the deflated balloon can typically be folded in such a manner as to have an outside diameter that is approximately the same as that of the catheter shaft 22. It will further be appreciated that the length and diameter of the balloon 30 may vary significantly from that illustrated in FIG. 1 without departing from the scope of the current invention.

The balloon 30 may be attached to the distal end 28 of the catheter shaft 22 using various techniques and configurations known in the art. In the embodiment shown in FIG. 1, an epoxy adhesive is used to connect the proximal end 37 of the balloon directly to the exterior surfaces of the guidewire tubular member 38 and the inflation/deflation lumens where they extend from the end of the catheter shaft. This allows the proximal end 37 of the balloon to butt up against the distal end 28 of the shaft as shown. It will be understood that the lumens are typically protected (e.g., with removable mandrels) during the joining procedure to ensure that adhesive does not block the lumen openings. The distal end 31 of the balloon is connected with a fluid-tight seal to the outside (i.e., radial) surface of the guidewire tubular member 38, which extends well beyond the distal end of the catheter shaft and passes through the interior of the balloon 30 as shown. The distal end 40 of the guidewire 32 can be seen exiting from the distal end of the guidewire tubular member 38, which typically marks the distal end of the catheter. The inflation/deflation lumens of the catheter, as described in greater detail below, empty from the distal end 28 of the catheter shaft 22 into the balloon interior 42, thereby allowing inflation and deflation of the balloon 30 by selectively introducing and withdrawing fluid through the second port 36 of the access fitting 26.

In order to achieve inflation/deflation time performance similar to that of conventional coaxial catheters, while at the same time achieving the distal flexibility, and hence trackability, characteristic of a multi-lumen catheter, the catheter 20 of the current invention has a shaft 22 with a unique hybrid design including a proximal portion 44 having a coaxial configuration disposed toward the proximal end 24 of the shaft, a distal portion 46 having a multi-lumen configuration disposed toward the distal end 28 of the shaft, and a transitional portion 48 disposed therebetween. Typically, although not always, the proximal portion 44 constitutes a majority of the catheter shaft's overall length, while the distal portion 46 constitutes a minority of the catheter shaft's overall length. The length of the transitional portion 48 is as short as possible, and is typically less than the length of the other two portions 44 and 46.

Figure 2:
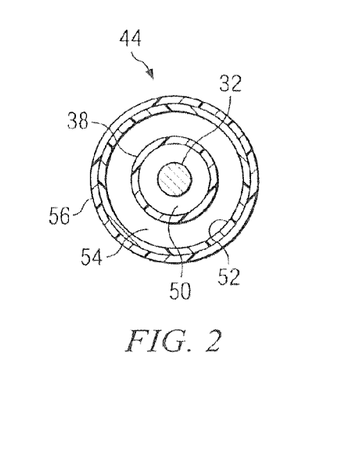
FIG. 2 is a cross-sectional end view of the proximal portion of the catheter shaft taken along the line 2-2 of FIG. 1.

Referring now to FIG. 2, there is illustrated a representative lateral cross-section of the proximal portion 44 of the catheter shaft 22, i.e., the portion having a coaxial configuration of the guidewire lumen and the inflation/deflation lumen. It will be appreciated that, for purposes of illustration, the wall thicknesses of the various tubular members may not be shown to scale in FIGS. 1-7, and the spacings between the various tubular members and around the guidewire may be exaggerated for clarity. The shaft proximal portion 44 has a proximal end at the proximal end 24 of the shaft and a distal end abutting the shaft transitional portion 48. The proximal portion 44 includes the guidewire tubular member 38 centrally disposed therewithin. The bore of the guidewire tubular member 38 defines the guidewire lumen 50 for slidably receiving the guidewire 32. The guidewire tubular member 38 is, in turn, coaxially disposed within the bore of an outer tubular member 52. It will be appreciated that the guidewire tubular member 38 may be free to "float" within the outer tubular member 52, i.e., there may be no rigid connection between the guidewire tubular member and outer tubular member along the proximal portion 44. The generally annular space disposed between the outer surface of the guidewire tubular member 38 and the inner surface of the outer tubular member 52 constitutes a proximal inflation/deflation lumen 54 for the conveyance of balloon inflation fluids. Accordingly, the outer tubular member 52 must be strong enough to withstand the balloon's maximum inflation pressure without bursting, and the guidewire tubular member 38 must be strong enough to withstand the balloon's maximum inflation pressure without collapsing.

The tubular members 38 and 52 of the proximal portion 44 may be formed of suitable materials such as plastic, elastomers, metal or metal alloy. For some catheters, the outer tubular member 52 may be formed of Nylon-11 loaded with approximately 20% bismuth by weight (to provide partial radiopacity) and the guidewire tubular member 38 may be formed of polyimide plastic, which is stronger but less flexible than Nylon-11. However, for small diameter catheters, e.g., those having an outside diameter of about 5 French or smaller, it is preferred to use higher strength materials than Nylon-11 for both of the tubular members 38 and 52 in order to keep their wall thicknesses as low as possible, and also to provide adequate torsional stiffness to the overall shaft 22. In preferred embodiments, both of the tubular members 38 and 52 are made of polyimide plastic.

The outer tubular member 52 may be sheathed in a jacket 56 made of a different material. Typically, the jacket 56 is not used to provide additional structural strength, but rather to change certain characteristics of the proximal portion 44 (i.e., as compared to the characteristics of the outer tubular member 52 alone). For example, ordinary polyimide plastic is relatively radiotransparent, and not easily loaded with radiopacifiers. Thus, where both tubular members 52 and 38 are made of polyimide plastic, the jacket 56 may be made of a radiopaque material to make the proximal portion of the catheter shaft more visible by radiography. In other examples, the proximal jacket 56 may be made of a material that provides a smooth exterior surface that minimizes the tendency for blood cells to accumulate thereupon and/or of a hydrophilic material that exhibits lubricity when it comes into contact with blood. The jacket 56 may be extruded or co-extruded around the outer tubular member 52 during its manufacture, or it may be bonded to the outer tubular member by thermal-compression molding or similar processes at a later time. In a preferred embodiment, the proximal portion jacket 56 is formed of polyether block amide (PEBA) thermoplastic elastomer, such as that sold under the trademark Pebax® PEBA elastomers such as Pebax® may be readily loaded with radiopacifiers, e.g., bismuth, and are available in plasticizer and additive-free medical grades having nominal hardnesses (Shore D method) ranging from about Shore D 25 to about Shore D 72. In portions of the catheter where maximum flexibility is not required, e.g., in the proximal portion 44, jackets made from a relatively hard PEBA formulation appears to have advantages. Thus, in another preferred embodiment, the jacket 56 for the proximal portion 44 of the catheter is a PEBA elastomer having a nominal Shore D hardness within the range from about Shore D 55 to about Shore D 72. In a more preferred embodiment, the proximal portion jacket 56 is made of Pebax® brand grade 7233 PEBA loaded with approximately 20% (by weight) bismuth (for partial radiopacity).

Figure 3:
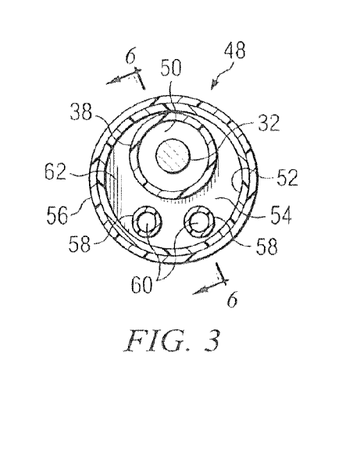
FIG. 3 is a cross-sectional end view of the transitional portion of the catheter shaft taken along the line 3-3 of FIG. 1.

Referring now to FIG. 3, there is illustrated a lateral cross-section of the transitional portion 48 of the catheter shaft 22, i.e., the portion wherein the shaft's internal configuration transitions from the coaxial configuration of the shaft proximal portion 44 into the multi-lumen configuration of the shaft distal portion 46. The shaft transitional portion 48 has a proximal end abutting the shaft proximal portion 44 and a distal end abutting the shaft distal portion 46. The cross-section illustrated in FIG. 3 is taken approximately midway through the shaft transitional portion 48, facing toward the distal end 28 of the catheter. The shaft transitional portion 48 includes the guidewire tubular member 38 (and its associated guidewire lumen 50) disposed within the bore of the outer tubular member 52. At the junction between the proximal and transitional shaft portions 44 and 48, the guidewire tubular member 38 is disposed in the center of the bore of the outer tubular member 52. However, as the guidewire tubular member 38 extends through the transitional portion 48 toward the distal end 28 of the shaft, it may be progressively displaced to one side of the bore, thereby transforming the cross-section of the proximal inflation/deflation lumen 54 from the generally annular shape shown in FIG. 2 to the generally crescentic (i.e., crescent-like) shape shown in FIG. 3. The transitional portion 48 further includes one or more distal tubular members 58 disposed in the proximal inflation/deflation lumen 54 between the guidewire tubular member 38 and the outer tubular member 52. These distal tubular members 58 extend from the shaft transitional portion 48 all the way through the shaft distal portion 46 to the balloon 30. The bores of these distal tubular members 58 define distal inflation/deflation lumens 60. It will be appreciated that the inner diameters of the distal tubular members 58 are significantly smaller than the inner diameter of the outer tubular member 52, and that the combined cross-sectional areas of all the distal inflation/deflation lumens 60 are significantly smaller than the cross-sectional area of the proximal inflation/deflation lumen 54. The proximal ends of the distal inflation/deflation lumens 60 are in fluid communication with the proximal inflation/deflation lumen 54. At a position between the proximal ends of the distal tubular members 58 and the junction between the transitional and distal shaft portions 48 and 46, the proximal inflation/ deflation lumen 54 is plugged with a fluid-tight barrier 62. The guidewire tubular member 38, the distal tubular members 58, and their respective lumens 50 and 60 continue through the barrier 62 and into the distal portion 46 of the shaft. The outer tubular member 52 continues past the barrier 62, but terminates at the junction between the transitional and distal shaft portions 48 and 46. If present in the shaft proximal portion 44, the exterior jacket 56 sheathing the outer tubular member 52 may continue onto at least a portion of the shaft transitional portion 48.

The distal tubular members 58 may be formed of suitable materials such as plastic, elastomers, metal or metal alloy. For small diameter catheters, it is preferred to use high strength materials for the distal tubular members in order to keep their wall thicknesses as low as possible, and also to provide adequate torsional stiffness to the shaft distal portion 46. In preferred embodiments, the distal tubular members 58 are made of polyimide plastic. The barrier 62 may be formed of any material that is both pressure-resistant and capable of forming a fluid-tight bond with the materials used for the various tubular members. In one embodiment, a two-part, medical grade epoxy resin is used for the barrier 62. In other embodiments, other known fluid-resistant adhesives or resins may be used.

Figure 4:
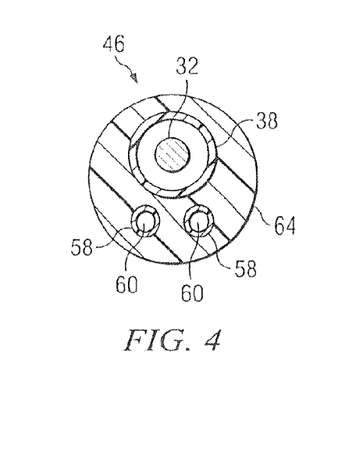
FIG. 4 is a cross-sectional end view of the distal portion of the catheter shaft taken along the line 4-4 of FIG. 1.

Referring now to FIG. 4, there is illustrated a representative lateral cross-section of the distal portion 46 of the catheter shaft 22, i.e., the portion having a non-coaxial, multi-lumen configuration. The shaft distal portion 46 has a proximal end abutting the shaft transitional portion 48 and a distal end at the distal end 28 of the shaft. The shaft distal portion 46 includes the guidewire tubular member 38, the non-coaxial distal tubular members 58, and their respective lumens 50 and 60 therewithin. The guidewire 32 may pass through the guidewire lumen 50, and inflation liquids may be conveyed through the distal inflation/deflation lumens 60. However, the outer tubular member 52 is not present in the shaft distal portion 46 to encase the other tubular members. Instead, the guidewire tubular member 38 and the distal tubular members 58 are encased in a distal body 64 formed of a suitable material such as extruded or molded plastic or elastomer. Since the tubular members 38 and 58 in the shaft distal portion 46 are smaller in diameter than the outer tubular member 52 of the shaft proximal portions 44, then, all other things being equal, the shaft distal portion will be inherently more flexible than the shaft proximal portion. Further, since the balloon inflation pressure is confined entirely within the distal inflation/deflation lumens 60, the distal body 64 is not required to have pressure-resisting strength. Thus, the material used for the distal body 64 is preferably more flexible than that used for the outer tubular member 52. Since the trackability characteristics of the catheter 20 are largely dependent on the flexibility of its shaft distal portion 46, the combination of smaller tubular members and softer body material in the shaft distal portion may result in significantly improved trackability for the catheter. Further, if the material used for the distal body 64 has satisfactory exterior surface characteristics, then an exterior jacket may not be required.

In a preferred embodiment, the distal body 64 is formed of a plastic or elastomer material that can be molded around the tubular members 38 and 58 by thermal-compression molding, i.e., using pressure and heat. In one embodiment, the distal body is formed of a polyether block amide (PEBA) thermoplastic elastomer such as Pebax® brand PEBA. PEBA thermoplastics may be molded using pressure and heat. Since flexibility is desirable for the shaft distal portion 46, using a relatively soft PEBA formulation for the distal body 64 appears to have advantages. Thus, in another preferred embodiment, the distal body 64 is made of a PEBA elastomer having a nominal Shore D hardness within the range from about Shore D 25 to about Shore D 54. In a more preferred embodiment, the distal body 64 is made of Pebax® brand grade 4033 PEBA with approximately 20% (by weight) bismuth.

Figure 5:
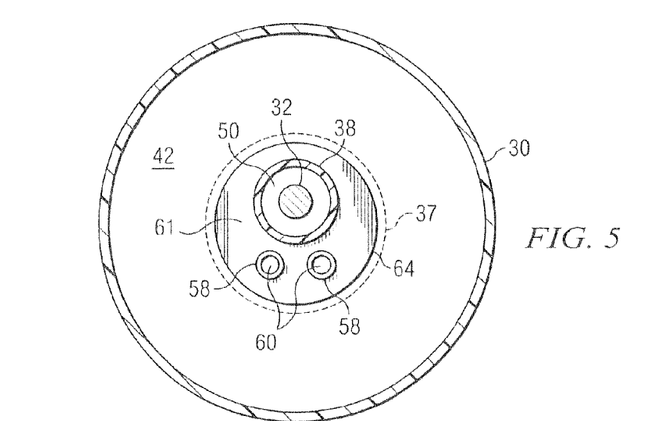
FIG. 5 is a cross-sectional end view through the balloon portion of the catheter taken along the line 5-5 of FIG. 1.

Referring now to FIG. 5, there is illustrated a representative lateral cross-section of the catheter 20 taken through the inflated dilation balloon 30. The cross-section illustrated in FIG. 5 is taken facing toward the distal end 28 of the catheter shaft 22 and the proximal end 37 of the balloon, which although not in the actual plane of the cross-section, are nonetheless visible in the field of view. The guidewire tubular member 38 and its lumen 50 pass entirely through the balloon 30, however the distal tubular members 58 terminate near the distal end 28 of the catheter, and their respective distal inflation/deflation lumens 60 are in fluid communication with the balloon interior 42. The epoxy adhesive seal 61 joining the proximal balloon end 37 to the exterior surfaces of the guidewire tubular member 38 and distal tubular members 58 is visible at the neck of the balloon, but it doesn't extend into the main body of the balloon. Thus, the combination of the proximal and distal inflation/deflation lumens 54 and 60 provides a continuous fluid channel through the catheter shaft 22 between the access fitting 26 on the proximal end 24 and the balloon interior 42 on the distal end 28. This allows the balloon 30 to be selectively inflated or deflated via the second port 36 of the access fitting 26.

Figure 6:
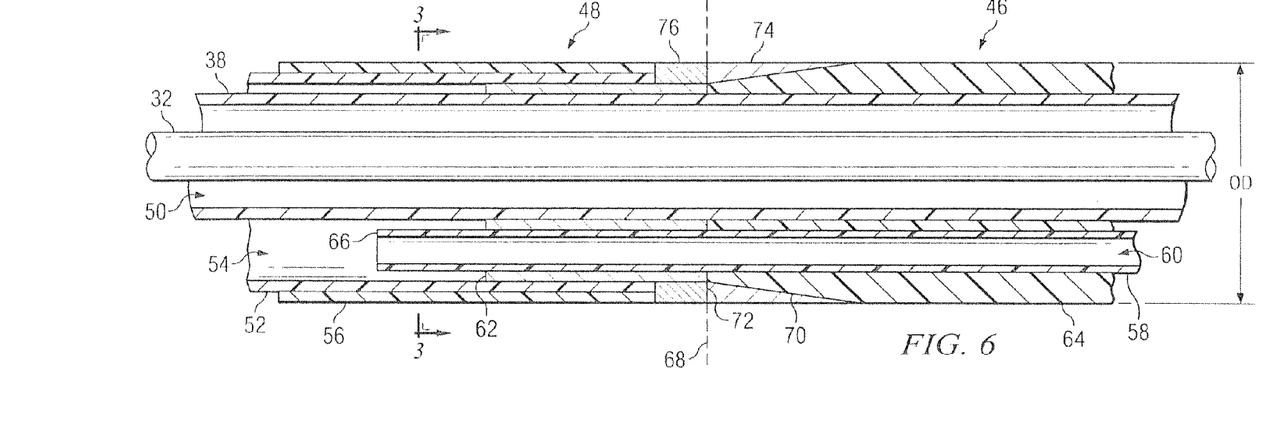
FIG. 6 is an enlarged cross-sectional side view of the transitional and distal portions of the catheter shaft taken along line 6-6 of FIG. 3.

Referring now the FIG. 6, there is illustrated a longitudinal cross-section through parts of the shaft transitional portion 48 and the shaft distal portion 46 showing further details of the transition region. In this embodiment, the guidewire tubular member 38 is upwardly displaced within the bore of the outer tubular member 52, and the proximal ends 66 of the distal tubular members 58 are disposed in the proximal inflation/deflation lumen 54 between the guidewire tubular member and the outer tubular member (it will be appreciated that only one of the two distal tubular members 58 is visible in FIG. 6). A fluid-tight barrier 62 is formed between the guidewire, outer, and distal tubular members 38, 52 and 58 at a position between the proximal ends 66 of the distal tubular members 58 and the junction (denoted by broken line 68) between the shaft transitional and distal portions 48 and 46. The barrier 62 thus plugs the proximal inflation/deflation lumen 54 in the distal direction, but leaves the distal inflation/deflation lumens 60 open and in fluid communication with the proximal inflation/deflation lumen. The outer tubular member 52 and its jacket 56 continue past the barrier 62, but each terminate at or near the junction 68. The guidewire tubular member 38, the distal tubular members 58, and their respective lumens 50 and 60 continue through the barrier 62 and into the distal portion 46 of the shaft. The guidewire tubular member 38 and the distal tubular members 58 are held in position in the shaft distal portion 46 by the surrounding distal body 64.

Referring still to FIG. 6, in embodiments for use with extremely high pressure fluids, a pressure deflector ring 76 may be provided at the distal end of the transitional portion 48. The pressure deflector ring is typically added onto the transitional portion 48 after the jacket 65 has been added, but prior to joining to the distal shaft portion 46. The pressure deflector ring 76 is dimensioned to have a diameter and thickness that matches the diameter and thickness of the combined outer tubular member 52 and jacket 56. Preferably, the pressure deflector ring 76 is formed "in-place" on the transitional portion 48 using thermal compression molding from PEBA thermoplastic or other T-C moldable material. Alternatively, the pressure deflector ring 76 may be a discrete article formed of suitable material, e.g., nylon or polyimide, and attached to the shaft by adhesive or other known bonding techniques. The pressure deflector ring 76 serves to prevent any high pressure fluid that may leak along the boundary between the fluid barrier 62 and the outer tubular member 52 and reach the junction 68 from "backtracking" into the boundary between the outer tubular member and the jacket 56. If high pressure fluid enters beneath the jacket 56, it can cause undesirable delamination of the jacket.

As best seen in FIG. 6, it is preferable that the outside diameter (denoted OD) of the catheter shaft 22 be substantially constant across region near the junction 68. However, in some embodiments, the proximal end 70 of the distal body 64 may be tapered to fit into the extreme distal end 72 of the outer tubular member 52 (or pressure deflector ring 76, if present) during assembly (e.g., to assist in centering the two portions 48 and 46). In such embodiments, a filler band 74 may be added to the shaft 22 after assembly of the distal portion 46 to the transitional portion 48. The filler band 74 may be made of a suitable material that is compatible with the adjacent jacket 56 and distal body 64. The material of the filler band 74 may be the same as that of the jacket 56 or distal body 64, or it may be a different material altogether. Preferably, the material of the filler band will be a plastic or elastomer material that can be molded around perimeter of the assembled catheter shaft 22 using pressure and heat. In one preferred embodiment, the filler band 74 is formed of a polyether block amide (PEBA) thermoplastic elastomer such as Pebax® brand PEBA.

Figure 7:
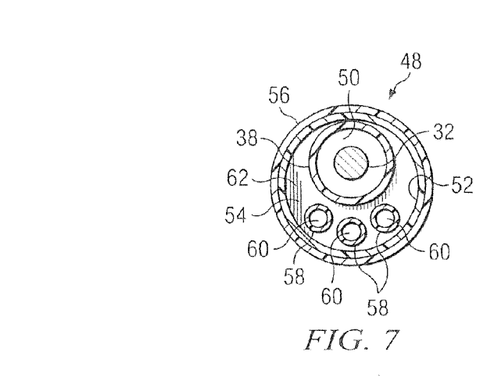
FIG. 7 is a cross-sectional view of the distal portion of the catheter shaft, similar to FIG. 4, in accordance with another embodiment.

Referring again to FIG. 3, the transitional distal portion 48 of the illustrated embodiment includes two distal tubular members 58 of equal size disposed adjacent to the one another and to the guidewire tubular member 38 within the bore of an outer tubular member 52. This structure facilitates transition from a coaxial lumen configuration to a multi-lumen configuration having dual inflation/deflation lumens. In other embodiments, it may be desirable to utilize transitional portions having one, two, three or more distal tubular members to support multi-lumen distal configurations having one, two, three or more inflation/deflation lumens. For example, referring now to FIG. 7, there is illustrated a lateral cross-section through the shaft transitional portion 48 of an alternative embodiment including a guidewire tubular member 38 and three distal tubular members 58 disposed within the bore of an outer tubular member 52. This structure facilitates transition from a coaxial lumen configuration to a multi-lumen configuration having triple inflation/deflation lumens. It will be appreciated that the remainder of this embodiment's structure is substantially similar to that of the previously described embodiments.

While catheters in accordance with the current invention may be constructed with a distal portion 46 of practically any length, the currently preferred design comprises a distal portion having a length of approximately 30 cm, regardless of the overall length of the catheter shaft. Currently preferred overall catheter shaft lengths fall within the range from about 40 cm. to about 150 cm. Thus, the relative length of the distal portion 46 (i.e., expressed as a percentage of overall catheter shaft length) for the current invention may fall within the range from about 20% to about 75% of the total length of the catheter shaft.

It will be appreciated that, because the coaxial structure of the proximal portion 44 does not extend all the way to the distal end of the shaft 22, the stiffness inherent in its coaxial design does not significantly affect the trackability of the catheter (which, as previously described, is largely governed by the flexibility of the distal end portion 46). Further, the multi-lumen distal portion 46 of the shaft 22, while not adversely affecting the inflation/deflation time performance of the catheter 20 in any significant way, is significantly more flexible relative to the coaxial proximal portion 44. Since the distal portion 46 is disposed at the distal end 28 of the shaft 22, i.e., the end most related to catheter trackability, this results in the catheter 20 exhibiting trackability characteristics that approximate those of a conventional multi-lumen catheter, and which are significantly better than conventional coaxial designs.

Since the transitional portion 48 of the shaft 22 is relatively short and located away from the distal end 28, it has relatively little effect on either the inflation/deflation time performance or the trackability of the catheter 20. Rather, the transitional portion 48 serves primarily to provide mechanical strength, alignment and pressure-tight fluid communication between the respective tubular members and lumens of the catheter shaft's proximal and distal portions 44 and 46.

Figure 8A:
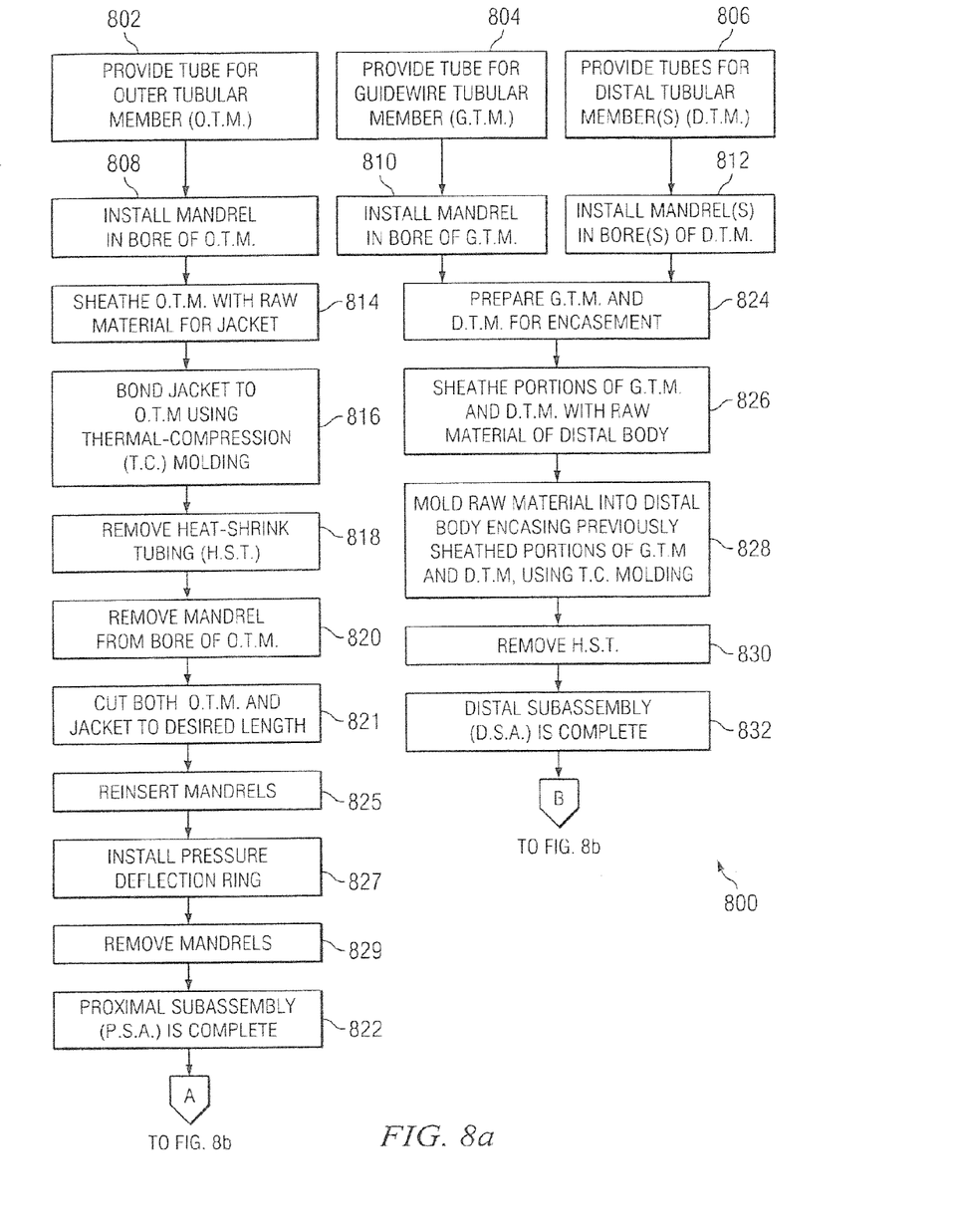
FIGS. 8a and 8b are a flow chart showing a method for manufacturing a hybrid catheter shaft in accordance with another embodiment.
Figure 8B:
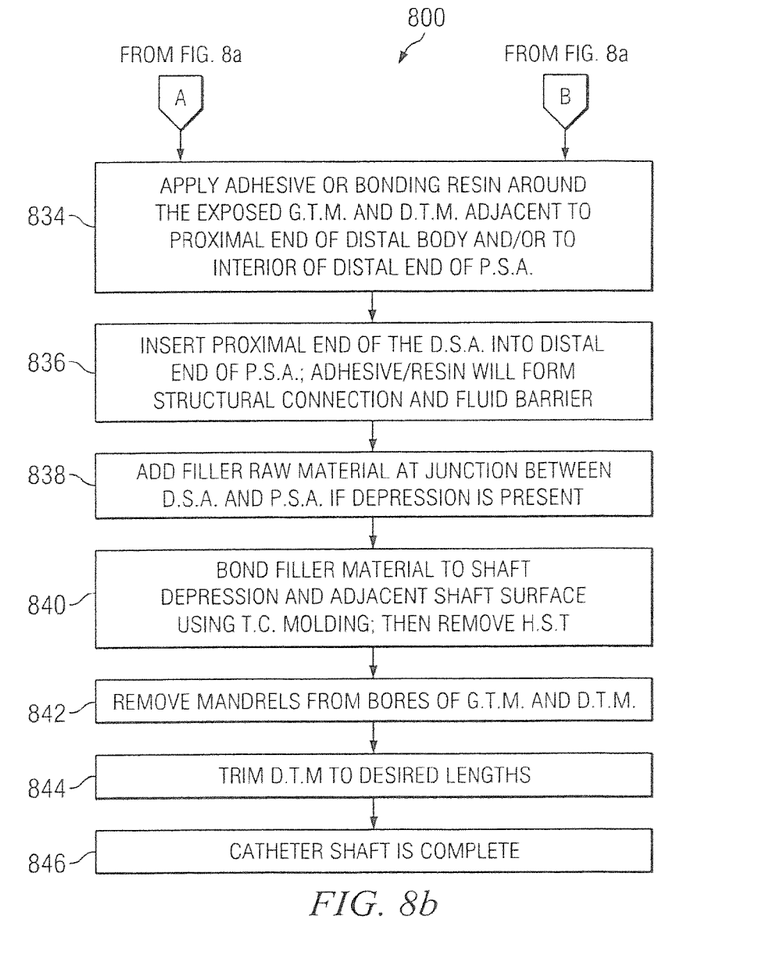

Referring now to FIGS. 8a and 8b, there is illustrated a method for manufacturing a catheter shaft for a balloon dilation catheter in accordance with another embodiment. The method of manufacture 800 begins with providing tubes for the outer tubular member, guidewire tubular member and distal tubular member as represented by blocks 802, 804 and 806, respectively. The various tubular members may be made of plastics or other materials as previously described. In preferred embodiments, one or all of the outer tubular member, guidewire tubular member and distal tubular members are made from polyimide plastic. Next, a mandrel made of steel or other noncompressible material is inserted into the bore of each of the tubes as shown in blocks 808, 810 and 812, respectively. The outer diameter of each mandrel is selected to slip closely within the bore of its respective tubular member, thereby providing support for the walls of the tubular member during subsequent processing steps, and ensuring that unwanted materials do not enter the bores of the tubular members during subsequent processing steps.

As the method 800 continues, each of the tubular members requires additional processing. For convenience, the following description will first describe the additional processing of the outer tubular member to form a proximal subassembly, then the processing of the remaining tubular members. However, it will be appreciated that the order of processing these tubular members may be changed without departing from the scope of the invention. As shown in block 814, the outer tubular member is next loosely sheathed with a suitable jacket raw material, e.g., PEBA thermoplastic elastomer. Such jacket material is often supplied in the form of an extruded tube that may be slipped over the outer tubular member, however, other forms of jacket raw material may be used. Next, as shown in block 816, the jacket material is bonded to the exterior of the outer tubular member using thermal compression molding or other known bonding techniques. In thermal compression molding, a combination of heat and pressure causes the jacket material to "flow" and adhere to the exterior of the outer tubular member. In a preferred embodiment, the thermal compression molding is accomplished by placing a length of heat-shrink tubing over the previously assembled jacket raw material, outer tubing member and mandrel, then heating this assembly in an oven. The heat from the oven serves to soften the jacket material so that it may flow, while at the same time the heat causes the heat-shrink tubing to shrink, thereby compressing the softened jacket material tightly against the exterior or the outer tubular member. The mandrel inside the bore of the outer tubular member prevents the collapse of the tubing walls even though they are subjected to considerable compression forces during the molding process. The compression molding provided by the heat-shrink tubing when heated is very uniform, thereby avoiding the formation of seam lines or any other surface irregularities on the surface of the jacket that might result from other molding techniques. After the jacket has been bonded to the exterior of the outer, tubular member, the heat-shrink tubing may be removed from the assembly, as indicated in block 818. Of course, in embodiments which do not include the exterior jacket, the operation shown in blocks 814, 816 and 818 may be omitted. After jacketing, the mandrel may be removed from the outer tubular member as shown in block 820. The outer tubular member and jacket, if present, may next be cut to their final lengths as shown in block 821. If desired, a pressure deflector ring may be added to the distal end of the subassembly at this point by first reinserting the mandrels (block 825), then installing the pressure deflector ring using thermal compression molding (or alternatively, by bonding a discrete ring to the subassembly) (block 827) and then removing the mandrels again (block 829). Preparation of the proximal subassembly is then complete as indicated in block 822.

The method 800 for constructing the catheter shaft now continues with further details of the construction of a distal subassembly. First, the guidewire tubular member and distal tubular members, with their respective mandrels installed as shown in blocks 810 and 812, are prepared for encasement in the distal body of the shaft, as shown in block 824. This preparation may include cutting the tubes to a predetermined length for assembly. Typically, the guidewire tubular member will be much longer than the distal tubular members with portions of the guidewire tubular member extending past the distal tubular member in both the proximal and distal directions. Next, as shown in block 826, portions of the guidewire tubular member and distal tubular members are loosely sheathed with the raw material to be used for the distal body. It is important to note that substantial portions of the guidewire tubular member and distal tubular member are not sheathed with this material as they will remain unencased in the distal body. In particular, the proximal ends of the distal tubing members and of the guidewire tubular member will be left unsheathed (it being understood that the unsheathed proximal end of the guidewire tubular member will be much longer than the unsheathed proximal end of the distal tubing members), and the distal end of the guidewire tubular member will be left unsheathed for later connection to the balloon. In a preferred embodiment, the raw material for the distal body is provided in the form of an extruded plastic tube that can be slipped over portions of the guidewire tubular member and distal tubular members, which are then positioned relative to one another and relative to the tube as previously described. In a preferred embodiment, the sheathing material is a PEBA thermoplastic elastomer.

Next, as shown in block 828, the distal body raw material is molded around the sheathed portions of the guidewire tubular member and distal tubular members using thermal compression molding to form the distal body. As previously described, this thermal compression molding may be accomplished by slipping a length of heat-shrink tubing over the previously assembled guidewire tubular member, distal tubular members and sheathing material, and then heating the entire assembly in an oven. The heat will soften the distal body raw material allowing it to flow between and around the tubing members under the pressure generated by the contracting heat-shrink tubing. The guidewire tubing member and distal tubing member are protected from collapse during the thermal compression molding by the presence of the mandrels within their respective bores. As previously described, the heat shrink tubing provides exceptionally smooth surface finish on the final molded distal body. After the thermal compression molding, the heat-shrink tubing may be removed as shown in block 830. Finally, any required trimming of the exposed ends of the tubular members may be performed to complete the distal subassembly as indicated in block 832. It will be appreciated that construction of the proximal subassemblies and the distal subassemblies are essentially independent of one another such that it makes no difference which subassembly is completed first in the method 800.

Once a proximal subassembly and a distal subassembly are available, final assembly may proceed as indicated in block 834. In final assembly, an adhesive or bonding resin, e.g., a two-part medical grade epoxy, is applied to the distal subassembly around the exposed guidewire tubular member and distal tubular members in the area immediately adjacent to the proximal end of the distal body. Adhesive may also be applied to the interior distal end of the proximal subassembly. Next, as shown in block 836, the proximal ends of the guidewire tubular member and distal tubing members (of the distal subassembly) are inserted into the bore of the outer tubular member (of the proximal subassembly) until the adhesive-coated region adjacent to the distal body abuts against the distal end of the proximal subassembly. This adhesive will form the fluid-tight barrier filling the distal part of the proximal inflation/deflation lumen of the shaft, while at the same time providing the structural connection between the proximal subassembly and the distal subassembly. Since the mandrels remain in place within the guidewire tubular member and the distal tubular members during the bonding process, no adhesives are able to enter the bores of these tubes and cause an undesired obstruction.

In a preferred embodiment, the proximal end of the distal subassembly may be slightly tapered prior to final assembly to facilitate the centering of the distal subassembly in the open end of the proximal subassembly. In such embodiments, the taper may result in the creation of an undesirable seam, gap or depression on the surface of the shaft at the joint between the proximal subassembly and the distal subassembly. As shown in block 838, a band of filler material may be added into the gap or depression at the joint between the distal subassembly and the proximal subassembly to smooth the exterior of the shaft. This filler may be applied through the use of thermal compression molding by first slipping a tube of raw plastic material over the uneven region, then slipping a length of heat-shrink tubing over the filler material and surrounding shaft, and then heating it in an oven. As previously explained, the raw filler material will be softened by the heating, and the heat-shrink tubing will then contract to provide pressure molding that bonds the filler material to the shaft surface and eliminates any unevenness in the shaft surface formed during final assembly. This method of assembly will result in the exterior surface of the catheter shaft being very smooth around the junction area.

After all thermal compression molding is completed, the mandrels may be removed from the guidewire tubular member and the distal tubular members as indicated in block 842. Next, any final trimming of the distal tubular members to desired lengths may be performed as shown in block 844, completing construction of the catheter shaft as shown in block 846. The catheter shafts manufactured using this method may subsequently be attached to dilation balloons and access fittings to manufacture complete catheter assemblies, or alternatively, they may be sold as components for use by others in constructing their own catheters. It will be appreciated that while the assembly method 800 described above is a preferred method of constructing the hybrid catheter shafts and catheters previously described in connection with FIGS.

What is claimed is:

1. A balloon catheter adapted to be used with a guidewire, the catheter comprising:
   an elongated catheter shaft including at least one lumen;
   a balloon attached to the distal end of the catheter shaft; and
   a guidewire tubular member associated with the catheter shaft, said guidewire tubular member extending from the proximal end of the shaft to the distal end of the shaft;
   wherein the catheter shaft transitions from a coaxial configuration at a proximal end of the catheter shaft to a non-coaxial, multi-lumen configuration at a distal end of the catheter shaft.

2. The catheter of claim 1, wherein the at least one lumen comprises a single proximal inflation/deflation lumen coaxial with the guidewire tubular member.

3. The catheter of claim 2, wherein the guidewire tubular member is disposed coaxially within the proximal inflation/deflation lumen.

4. The catheter of claim 2, further including at least one distal inflation/deflation lumen that is non-coaxial with the guidewire tubular member, wherein the proximal inflation deflation lumen is in fluid communication with the at least one distal inflation/deflation lumen for inflating and deflating the balloon.

5. The catheter of claim 4, further including a fluid-tight barrier for transitioning inflation fluid from the proximal inflation/deflation lumen to the distal inflation/deflation lumen.

6. The catheter of claim 4 including a plurality of distal inflation/deflation lumen.

7. The catheter of claim 1, wherein the guidewire tubular member is formed of one of a plastic, an elastomer, a metal, or a metal alloy.

8. The catheter of claim 7, wherein the guidewire tubular member is formed of a polyimide plastic.

9. The catheter of claim 1, wherein the catheter shaft is at least partially radiopaque.

10. A balloon catheter for use with a guidewire comprising:
    a catheter shaft with a proximal and distal end;
    a balloon attached to the distal end of the shaft;
    a guidewire lumen for housing the guidewire extending from the proximal end of the shaft to the distal end of the shaft; and
    at least one inflation/deflation lumen for delivering fluid to and from the balloon;
    wherein the guidewire lumen and the inflation/deflation lumen are coaxial at the proximal end of the catheter shaft and said lumens transition to a non-coaxial configuration at the distal end of the catheter shaft.

11. The catheter of claim 10, further including an outer tubular member defining a proximal inflation/deflation lumen, said outer tubular member formed of one of a plastic, an elastomer, a metal and a metal alloy.

12. The catheter of claim 11, further including at least one distal tubular member defining a distal inflation/deflation lumen, said distal tubular member formed of one of a plastic, an elastomer, a metal and a metal alloy.

13. The catheter of claim 12, further including a fluid-tight barrier for selectively diverting fluid between the outer tubular member and the distal tubular member for inflating and deflating the balloon.

14. The catheter of claim 10, further including a jacket surrounding a proximal portion of the guidewire lumen and the inflation/deflation lumen.

15. The catheter of claim 14, wherein the jacket is formed of a polyether block amide (PEBA) thermoplastic elastomer.

16. The catheter of claim 10, further including a distal body encasing a distal portion of the guidewire lumen and the inflation/deflation lumen.

17. The catheter of claim 16, wherein the distal body is formed of a plastic or an elastomer.

18. The catheter of claim 17, wherein the distal body is formed of a polyether block amide (PEBA) thermoplastic elastomer.

19. The catheter of claim 10, wherein the catheter shaft is more flexible at the distal end than at the proximal end.

20. A catheter shaft for use with a balloon catheter and a guidewire, said catheter shaft having a proximal end and a distal end, the distal end for attaching to the balloon, comprising:
    a guidewire tubular member for housing the guidewire extending from the proximal end of the shaft to the distal end of the shaft; and
    at least one inflation fluid tubular member at least partially defining an inflation/deflation lumen, said inflation/deflation lumen having a larger diameter at the proximal end of the shaft and a smaller diameter at the distal end of the shaft;
    wherein the guidewire tubular member and the inflation/deflation lumen are coaxial in the proximal end of the shaft and transition to a non-coaxial configuration at the distal end of the shaft, such that the distal end of the shaft is more flexible that the proximal end of the shaft.

* * * * *

UNITED STATES PATENT AND TRADEMARK OFFICE
CERTIFICATE OF CORRECTION

| | | |
|---|---|---|
| PATENT NO. | : 8,486,103 B2 | |
| APPLICATION NO. | : 13/188054 | |
| DATED | : July 16, 2013 | |
| INVENTOR(S) | : Lanny R. Pepper | |

It is certified that error appears in the above-identified patent and that said Letters Patent is hereby corrected as shown below:

In the Claims

Column 16, line 50, claim 20, please replace "that" with --than--.

Signed and Sealed this
Twentieth Day of May, 2014

Michelle K. Lee
*Deputy Director of the United States Patent and Trademark Office*